US00PP26908P3

(12) United States Plant Patent
Rat

(10) Patent No.: US PP26,908 P3
(45) Date of Patent: Jul. 5, 2016

(54) ***PAEONIA* PLANT NAMED 'RTPIV789-06'**

(50) Latin Name: ***Paeonia lactiflora*×*Paeonia lutea***
Varietal Denomination: RTPIV789-06

(71) Applicant: Thierry Rat, Moissac (FR)

(72) Inventor: Thierry Rat, Moissac (FR)

(73) Assignee: Planteck (CA)

( * ) Notice: Subject to any disclaimer, the term of this patent is extended or adjusted under 35 U.S.C. 154(b) by 234 days.

(21) Appl. No.: 13/998,811

(22) Filed: Dec. 9, 2013

(65) Prior Publication Data

US 2015/0163979 P1 Jun. 11, 2015

(51) Int. Cl.
*A01H 5/02* (2006.01)

(52) U.S. Cl.
USPC ..... Plt./316

(58) Field of Classification Search
USPC ..... Plt./316
See application file for complete search history.

*Primary Examiner* — June Hwu
(74) *Attorney, Agent, or Firm* — Cassandra Bright

(57) ABSTRACT

A new and distinct *Paeonia* cultivar named 'RTPIV789-06' is disclosed, characterized by distinctive bright pink, fully double, mildly fragrant flowers. Plants are vigorous, symmetrical with strong stems holding flowers above foliage, and with attractive foliage through the Fall. The new cultivar is a *Paeonia*, suitable for ornamental garden purposes.

1 Drawing Sheet

Latin name of the genus and species: *Paeonia lactiflora*× *Paeonia lutea.*

Variety denomination: 'RTPIV789-06'.

BACKGROUND OF THE INVENTION

The new cultivar is a product of a breeder program conducted by the inventor, Thierry Rat. This new variety, hereinafter referred to as 'RTPIV789-06', was discovered as part of a planned breeding program. The inventors, Thierry Rat crossed the seed parent *Paeonia lactiflora* 'Miss America', unpatented with the pollen parent, *Paeonia lutea* 'Chinese Dragon' during May of 2006. The resulting new variety was selected in a research nursery in Castel Sarrasin France during May of 2011.

After identifying the new variety as a potentially interesting selection, the inventor first organized propagation of 'RTPIV789-06' by tissue shoot culture, at a commercial laboratory in L'Assomption, Quebec, during September of 2011. The inventor continued controlled testing and propagation, assessing stability of the unique characteristics of this variety. Several generations have been reproduced and have shown that the unique features of this cultivar are stable and reproduced true to type.

SUMMARY OF THE INVENTION

The cultivar 'RTPIV789-06' has not been observed under all possible environmental conditions. The phenotype may vary somewhat with variations in environment such as temperature, day length, and light intensity, without, however, any variance in genotype. The following traits have been repeatedly observed and are determined to he the unique characteristics of 'RTPIV789-06' These characteristics in combination distinguish 'RTPIV789-06' as a new and distinct *Paeonia* cultivar:

1. Strong stems which hold the flowers uniquely erect and above the foliage.
2. Unique bright pink, fragrant and fully double flower.

3. Symmetrical, bushy plant shape.
4. Attractive foliage through Fall.

COMPARISON TO PARENT VARIETY

'RTPIV789-06' is similar in most horticultural characteristics to the seed parent variety *Paeonia lactiflora* 'Miss America'. Plants of the new cultivar 'RTPIV789-06' however, differ in the following characteristics:

1. 'Miss America' has a white, semi-double flowers, the new variety has a bright pink, fully double flower.
2. The new variety has stronger stems.
3. Foliage of the new variety is more finely cut.

'RTPIV789-06' is similar in most horticultural characteristics to the pollen parent variety *Paeonia lutea* 'Chinese Dragon'. Plants of the new cultivar 'RTPIV789-06' however, differ in the following characteristics:

1. 'Chinese Dragon' has a red, single to semi-double flowers, the new variety has a bright pink, fully double flower.
2. The new variety is a more herbaceous plant.
3. The new variety is more Winter hardy.

COMMERCIAL COMPARISON

'RTPIV789-06' can be compared to the commercial variety *Paeonia* 'Bartzella' unpatented. Plants of the new cultivar 'RTPIV789-06' are similar to plants of 'Bartzella' in most horticultural characteristics, as both are interspecific hybrid *Paeonias*. Plants of the new cultivar 'RTPIV789-06' however, produce bright pink flowers, whereas flower of 'Bartzella' are yellow with a red center.

'RTPIV789-06' can be compared to the commercial variety *Paeonia* 'Morning Lilac' unpatented. Plants of the new cultivar 'RTPIV789-06' are similar to plants of 'Morning Lilac' in most horticultural characteristics, as both are interspecific hybrid *Paeonias*. Plants of the new cultivar 'RTPIV789-06' however, produce fully double, bright pink flowers, whereas flower of 'Morning Lilac' are much lighter in color, with significantly less petals. Additionally, plants of the new variety have more secondary flower buds then 'Morning Lilac' plants.

BRIEF DESCRIPTION OF THE PHOTOGRAPH

The accompanying photograph in FIG. 1 illustrates in full color a typical plant of 'RTPIV789-06' grown outdoors in Moissac, France. The plant is approximately 6 years old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RTPIV789-06' plants grown outdoors in Moissac, France. Plants are approximately 6 years old, in a 2 gallon nursery container. Measurements and numerical values represent averages of typical plant types.

Botanical classification: *Paeonia lactiflora*×*P. lutea* 'RTPIV789-06'.

PROPAGATION

Typically by tissue shoot culture.

Root description: Freely branching storage root with numerous feeder roots.

PLANT

Growth habit: Compact and vigorous perennial herbaceous shrub. Symmetrical and rounded growth habit.

Height: Approximately 90 to 100 cm.

Plant spread: Approximately 125 cm.

Stems:

- *Length*.—Approximately 90 to 100 cm.
- *Diameter*.—Average 1.4 cm measured between first and second leaf.
- *Strength*.—Strong.
- *Internode length*.—Average 11 cm, highly variable.
- *Color*.—Near RHS Red-Purple 60A.

Texture: Glabrous.

FOLIAGE

Leaf: Alternate, bipinnately compound, with an overall ovate shape, which is wider than long. Average leaf 38 cm long and 39 cm wide. Leaf attitude erect.

Leaflets:

- *Shape*.—Broadly elliptic.
- *Quantity and arrangement*.—3 primary leaflet further divided into secondary leaflets of variable number and form. All leaflets sessile.
- *Average length*.—Central leaflet average 18 cm.
- *Average width*.—Central leaflet average 19 cm.

Individual leaflet blades:

- *Shape of blade*.—Broad elliptic, variably incised.
- *Apex*.—Broadly acuminate, often with emargination.
- *Base*.—Attenuate.
- *Margin*.—Deeply incised.
- *Texture of top surface*.—Glabrous.
- *Texture of bottom surface*.—Glabrous.
- *Appearance of top surface*.—Matte.
- *Appearance of bottom surface*.—Matte.
- *Aspect*.—Flat to very minutely reflexed downward.
- *Color*.—Upper side: Near RHS Yellow-Green 146A. Under side: Near RHS Greyed-Green 191A.
- *Venation*.—Type: Pinnate. Venation color upper side: Near RHS Yellow-Green 145A. Venation color under side: Near RHS Yellow-Green 145A.
- *Petiole*.—Length: Average 11 cm. Diameter: 0.8 cm. Color: Near RHS Red-Purple 60A. Texture: Glabrous, moderately glossy.

FLOWER

Natural flowering season: Flowers open approximately 60 days after bud break in early Spring. Continuous repeat flowering from Spring through Summer.

Inflorescence type and habit: Single, terminal or axillary flowers, fully double, irregularly rounded with tight petal whorl. Flower attitude erect.

Flower longevity on plant: Approximately 8 to 12 days on the plant.

Quantity of flowers: 4-7 per stem.

Flower size:

- *Diameter*.—Approximately 20 cm.
- *Depth*.—Approximately 11 cm. (Flower height).

Peduncle:

- *Length*.—Approximately 30 cm.
- *Diameter*.—Approximately 0.7 cm.
- *Color*.—Near RHS Yellow-Green 144A.
- *Strength*.—Strong.
- *Texture*.—Glabrous.

Petals:

- *Petal arrangement*.—Tight, irregular whorl of 70 to 75 full petals. Additional petaloid count variable.
- *Size*.—Length: Approximately 9.2 cm. Width: Approximately 7 cm.
- *Shape*.—Obovate.
- *Margin*.—Entire to sinuate.
- *Apex*.—Typically emarginate.
- *Base*.—Obtuse.
- *Texture*.—Smooth, glabrous all surfaces.
- *Aspect*.—Slightly ruffled, undulate.
- *Color*.—Petals: When opening: Upper surface: Near RHS Red-Purple 67B, occasionally some streaking near White 155B. Base Red-Purple 61A. Lower surface: Near RHS Red-Purple 67B, occasionally some streaking near White 155B. Base Red-Purple 61A. Fully opened: Upper surface: Near RHS Red-Purple 67B, occasionally some streaking near White 155B. Base Red-Purple 61A. Lower surface: Near RHS Red-Purple 67B, occasionally some streaking near White 155B. Base Red-Purple 61A.

Petaloids:

- *Type*.—Stamenoidal.
- *Quantity*.—Average 10 to 30.
- *Size*.—Length: Average 7.0 to 9.0 cm. Width: Average 0.5 cm to 1.0 cm.
- *Color*.—Near RHS Red-Purple 67B.

Bud:

- *Shape*.—Elongated globose.
- *Length*.—Approximately 4 to 5 cm.
- *Diameter*.—Approximately 3.5 cm.
- *Color*.—Near RHS Yellow-Green 144A.

Sepals:

*Quantity.*—5; 2 smaller and 3 larger.

*Length.*—Approximately 2.5 cm.

*Width.*—Approximately 4.0 cm.

*Shape.*—Obcordate to obovate.

*Aspect.*—Cupped.

*Apex.*—Mucronate.

*Margin.*—Entire. Color: Interior Surface: RHS Yellow-Green 144A, Red-Purple 67B flush. Exterior Surface: RHS Yellow-Green 144B, Red-Purple 67B flush.

*Texture.*—Glabrous.

Fragrance: Mild.

REPRODUCTIVE ORGANS

Stamens:

*Number.*—Approximately 10 fully developed. Many more poorly developed.

*Filament length.*—Approximately 2.2 cm.

*Filament color.*—Near RHS Red-Purple 60B.

Anthers:

*Length.*—1.8 cm.

*Shape.*—Elongated ovoid, some twisted or coiled.

*Color.*—Near RHS Yellow 6D.

*Pollen.*—Not observed to produce pollen.

Pistil:

*Type.*—Compound.

*Number of carpels.*—Average 6, variable.

*Length of carpel.*—Approximately 2.5 to 3.0 cm.

*Stigma.*—Shape: Claw shaped, acutely convex. Color: Near RHS Red-Purple 62A.

*Ovary color.*—Near RHS Green 142D.

OTHER CHARACTERISTICS

Disease and pest resistance: Not observed to be susceptible nor resistant to normal diseases and pests of *Paeonia lactiflora*×*Paeonia lutea.*

Temperature tolerance: Typically USDA Zones 3 to 9.

Fruit/seed production: Not observed.

What is claimed is:

1. A new and distinct cultivar of *Paeonia* plant named 'RTPIV789-06' as herein illustrated and described.

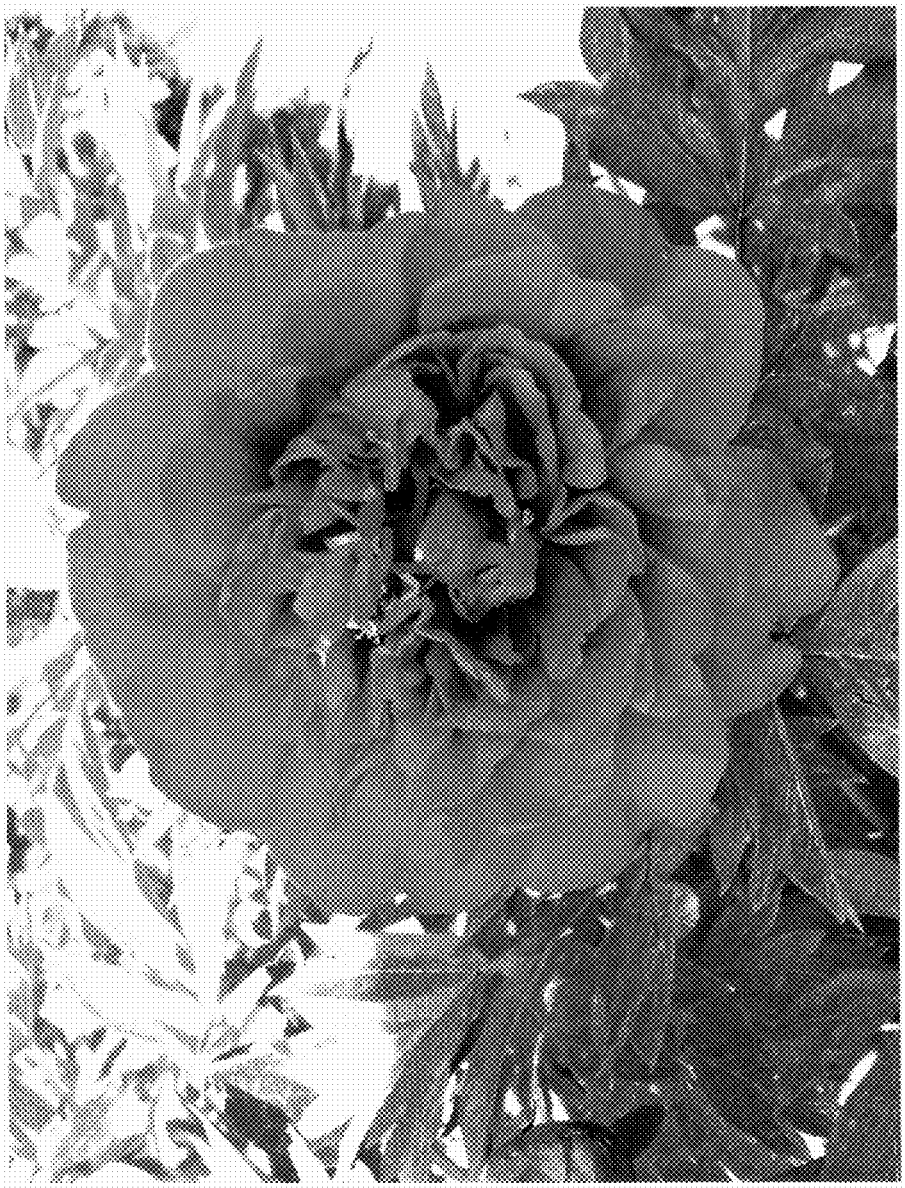

* * * * *